United States Patent [19]

Wilson et al.

[11] Patent Number: 4,656,036

[45] Date of Patent: Apr. 7, 1987

[54] ANTIBIOTICS TEJERAMYCIN AND PRODUCTION THEREOF

[75] Inventors: Kenneth E. Wilson, Westfield; Sheldon B. Zimmerman, Springfield, both of N.J.

[73] Assignee: Merck & Co., Inc., Rahway, N.J.

[21] Appl. No.: 690,715

[22] Filed: Jan. 11, 1985

Related U.S. Application Data

[63] Continuation of Ser. No. 446,154, Dec. 2, 1982, abandoned.

[51] Int. Cl.$^4$ .......................... A61K 35/74; C12P 1/06
[52] U.S. Cl. ..................................... 424/115; 435/169
[58] Field of Search ..................... 424/115; 435/169

[56] References Cited

U.S. PATENT DOCUMENTS 4,180,564 12/1979 Godfrey et al. ............... 424/118

Primary Examiner—Jerome D. Goldberg
Attorney, Agent, or Firm—Hesna J. Pfeiffer; Julian S. Levitt

[57] ABSTRACT

The antibiotics Tejeramycin are active against gram negative and gram positive infections, especially against *Pseudomonas aeruginosa*. The antibiotics Tejeramycin are produced by the aerobic fermentation of *Streptomyces griseus* ATCC No. 39208 or 39209 in an assimilable aqueous nutrient medium.

5 Claims, 1 Drawing Figure

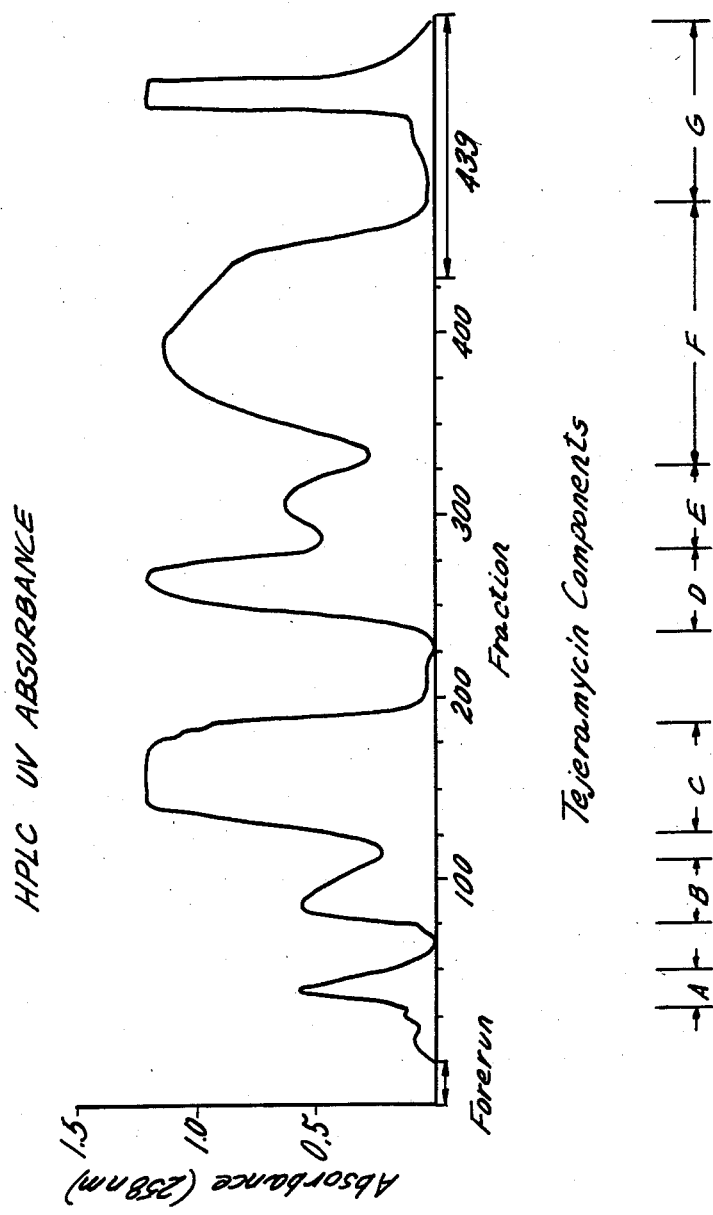

ANTIBIOTICS TEJERAMYCIN AND PRODUCTION THEREOF

This is a continuation of application Ser. No. 446,154, filed Dec. 2, 1982, now abandoned.

BACKGROUND OF THE INVENTION

The present invention is directed to the antibiotics Tejeramycin and a process for the production thereof.

In particular, this invention is directed toward the mixture of antibiotic components known collectively as Tejeramycin and individually as Tejeramycin—A, B, C, etc. produced by cultivating under aerobic conditions, *Streptomyces griseus* ATCC No. 39208 or 39209 in an assimilable aqueous nutrient medium.

The antibiotics Tejeramycin, collectively and individually, exhibit activity against both gram negative and gram positive infections. The antibiotics Tejeramycin are especially active against *Pseudomonas aeruginosa*.

BRIEF DESCRIPTION OF THE DRAWING

The FIGURE illustrates the UV absorbance at 258 nm of column effluent from the LiChroprep RP-18 chromatography described in Example 4. Regions of elution of Tejeramycin components A-G are indicated.

SUMMARY OF THE INVENTION

There is herein described the complex of antibiotics Tejeramycin and a process for their production which comprises cultivating *Streptomyces griseus* ATCC No. 39208 or 39209 in an aqueous assimilable nutrient medium at a temperature range of 26° to 30° C., a pH range of from 6.0 to 8.0 for at least 48 hours. The preferred conditions are a temperature of 28° C., pH of about 7.0 and optimum growth is reached after about 120 total hours.

DETAILED DESCRIPTION OF THE INVENTION

The antibiotics complex, Tejeramycin, is produced by the aerobic fermentation of *Streptomyces griseus* ATCC No. 39208 or 39209. The term "complex" as used herein refers to the mixture of coproduced individual antibiotic components which comprise Tejeramycin. The microorganism ATCC No. 39208 was isolated from soil in Venezuela, and a sample of this living organism has been deposited without restriction in, and made a part of, the American Type Culture Collection, Rockville, Md., from which it is available under Accession Number ATCC No. 39208

An examination of the cultural and morphological characteristics of *Streptomyces griseus* ATCC No. 39208 was made according to the method described in Bergey's *Manual of Determinative Bacteriology*, 8th Edition, The Williams and Wilkins Company, Baltimore, Md. The data shown below confirm the designation of the culture ATCC No. 39208 as a strain of *Streptomyces griseus*. Differences are minor and of a strain differentiating nature.

The cultural characteristics of *Streptomyces griseus* ATCC No. 39208 are as follows:

TABLE I
Taxonomy Data (V = vegetative growth; A = aerial mycelium; SP = soluble pigment)

TABLE I-continued
Taxonomy Data

Morphology: Sporophores are monopodially branched, forming tufts. Spore chains are straight to slightly flexuous. Spores are spherical to oval, 0.9μ in diameter to 0.9 × 1.2μ (970X). Spore surface as seen by transmission electron microscopy is smooth.

Oatmeal agar (ISP Medium 3)
V: Reverse - light brown
A: Powdery, tan edged with tannish yellow (2db)
SP: Light tan

Czapek Dox agar (sucrose nitrate agar)
V: Reverse - yellowish orange
A: Powdery, tannish-yellow; growth light in center and heavier on edges;
SP: Light tannish-yellow

Egg albumin agar
V: Reverse - grayish tan
A: Tan-yellow with a green cast (2db)
SP: Light tannish-yellow

Glycerol asparagine agar (ISP Medium 5)
V: Reverse - tan
A: Powdery, tan edged with tannish yellow
SP: Light tannish-yellow

Inorganic salts-starch agar (ISP Medium 4)
V: Reverse - tan
A: Powdery, tan edged with tannish yellow with greenish cast (2db)
SP: Light tannish-yellow

Yeast extract-malt extract agar (ISP Medium 2)
V: Reverse - tan
A: Powdery, tan edged with tannish-yellow with greenish cast (2db)
SP: Light tannish-yellow

Peptone-iron-yeast extract agar
V: Tan
A: Moderate, grayish
SP: Slight browning of medium
Melanin: None

Nutrient tyrosine agar
V: Reverse - cream colored
A: Whitish
SP: None

Tyrosine Agar (ISP Medium 7)
V: Greenish-tan
A: Cream-colored edged with light gray-green
SP: Pale tannish-yellow

Carbon utilization
Pridham-Gottlieb basal medium + 1% carbon source;
+ = growth; ± = growth poor or questionable;
− = no growth as compared to negative control
(no carbon source)

| Carbon source | Growth |
|---|---|
| Glucose | + |
| Arabinose | + |
| Cellulose | − |
| Fructose | + |
| Inositol | − |
| Lactose | + |
| Maltose | + |
| Mannitol | + |
| Mannose | + |
| Raffinose | ± |
| Rhamnose | + |
| Sucrose | ± |
| Xylose | + |

Temperature range (Yeast extract-dextrose + salts agar)
26° C. - Good growth with sporulation
37° C. - Good vegetative growth, scant aerial mycelia
50° C. - No growth
Oxygen requirement (Stab culture in yeast extract-dextrose + salts agar) - Aerobic.

All readings taken after three weeks at 28° C. unless noted otherwise. pH of all media approximately neutral (6.8–7.2).

Color number designations taken from Color Harmony Manual, 1958, 4th Edition, Container Corporation of America, Chicago, Ill.

The microorganism *Streptomyces griseus* ATCC No. 39209 is a naturally occurring isolate of ATCC No. 39208 and it possesses the same cultural characteristics.

It is to be understood that for the production of the antibiotics Tejeramycin, the present invention is not limited to the use of *Streptomyces griseus* ATCC No. 39208 or 39209. It is especially desired and intended that there be included within the scope of this invention, the use of natural or artificial mutants or variants produced from the described organism, or other variants of *Streptomyces griseus* ATCC No. 39208 or 39209 in so far as they can produce the antibiotics Tejeramycin or any one or more of the individual components of the Tejeramycin complex. The artificial production of mutant *Streptomyces griseus* from culture ATCC No. 39208 or 39209 may be achieved by a conventional operation such as x-ray or ultraviolet irradiation of the described culture, or by the use of chemical mutagens such as: nitrogen mustards, nitrosoguanidine and the like.

In a preferred embodiment of the present invention, the antibiotics Tejeramycin are produced by the aerobic cultivation of the microorganism *Streptomyces griseus* ATCC No. 39208 or 39209, at a temperature range of from 26° C. to 30° C., preferably 28° C. Generally, the composition of the nutrient medium may be varied over a wide range. The essential nutrient ingredients are: a carbon source and a nitrogen source. Other essential nutrients are provided via the mineral salts such as the chlorides, nitrates, sulfates, carbonates and phosphates of sodium, potassium, ammonium and calcium. The nutrient medium may also contain sources of inorganic trace elements such as magnesium, iron, copper, manganese, zinc, cobalt and the like. Cultivation has been found to be most productive in the pH range of from 6.0 to 8.0, most preferably at about 7.0.

Typical sources of carbon include: glucose, maltose, sucrose, dextrin, oil, starches, glycerol and the like. Typical nitrogen sources include: vegetable meals and extracts (e.g., malts, soy, cotton seed, figs, tomato, corn, etc.), animal viscera, various hydrolysates (e.g., casein, yeast, etc.) and fermentation by-products such as whole yeast and distillers solubles.

The maximum yield of the antibiotics Tejeramycin can be achieved within about 48 to 200 hours, usually in about 120 hours of fermentation under optimum conditions. The inoculum for the fermentation may be provided from vegetative growth in a medium which supports rapid growth of the organism.

Following fermentation, the accumulated antibiotics Tejeramycin may be recovered from the broth by conventional chromatographic means. Generally, the broth is filtered through a filter aid to remove suspended solids, the filtrate is adjusted in pH and chromatography is employed to separate the active components.

A number of different nutrient media may be employed in the fermentation of *Streptomyces griseus* ATCC No. 39208 or 39209, for the production of Tejeramycin antibiotics. Variation of the medium will vary the amount of individual components of the Tejeramycin complex produced. The preferred media compositions are set forth in Table II.

TABLE II

| Media Compositions | |
|---|---|
| KE | KEM |
| Dextrose 1 g/L | Maltose 10 g/L |
| Soluble Starch 10 g/L | Beef Extract 3 g/L |
| Beef Extract 3 g/L | Autolyzed yeast 5 g/L |
| Autolyzed yeast 5 g/L | NZAmine E 5 g/L |
| NZamine E 5 g/L | $MgSO_4$ $7H_2O$ 0.05 g/L |
| $MgSO_4$ $7H_2O$ 0.5 g/L | $Na_2HPO_4$ 0.190 g/L |
| $Na_2HPO_4$ 0.190 g/L | $KH_2PO_4$ 0.182 g/L |
| $KH_2PO_4$ 0.182 g/L | $CaCO_3$ 0.5 g/L |
| $CaCO_3$ 0.5 g/L | Distilled water pH 7-7.2 with NaOH |
| Distilled water pH7-7.2 with NaOH | |
| AK | KH |
| | Tomato Paste 20 g/L |
| Dextrose 10 g/L | Primary yeast 10 g/L |
| Asparagine 1 g/L | Starch 20 g/L |
| $KH_2PO_4$ 0.1 g/L | $CoCl_2$ $6H_2O$ 5 mg/L |
| $MgSO_4$ $7H_2O$ 0.5 g/L | Distilled water |
| Autolyzed yeast 0.5 g/L | pH 7.2–7.4 with NaOH |
| Trace Element Mix 10 ml/L | Trace Element Mix |
| Distilled water pH 7.2 | $FeSO_4$ $7H_2O$ 1 g/L |
| KW | $MnSO_4$ $4H_2O$ 1 g/L |
| Dextrose 20 g/L | $CuCl_2$ $2H_2O$ 25 mg/L |
| Bacto peptone 5 g/L | $CaCl_2$ 100 mg/L |
| Beef Extract 5 g/L | $H_3BO_3$ 56 mg/L |
| NaCl 5 g/L | $(NH_4)_6MO_7O_{24}$ $4H_2O$ 19 mg/L |
| Primary yeast 3 g/L | $ZnSO_4$ $7H_2O$ 200 mg/L |
| Distilled water | Distilled |
| pH 7.0 then | Deionized water |
| $CaCO_3$ 3 g/L | |

The terms "seed" and "production" media are employed as terms of art. Generally, a seed medium supports rapid growth of the microorganism and an aliquot (seed) of this medium is used to inoculate a production medium for a large scale fermentation. The preferred seed medium was KE. The best *Pseudomonas aeruginosa* activity for the Tejeramycin was derived from KW production medium. The best overall antibiotic activity was derived from KEM production medium.

The following examples describe the fermentation production and isolation of the antibiotics Tejeramycin. These examples are merely illustrative, they are not intended to limit the scope of this invention.

EXAMPLE 1

(A) *Streptomyces griseus* ATCC No. 39208 was used to inoculate, using aseptic techniques, a 250 ml baffled Erlenmeyer seed flask containing 54 ml of medium KE. The seed flask was shaken at 28° C. on a 220 rpm shaker (2" throw) for 24 hours. The seed medium was then stored without agitation at 4° C. for 24 hours. The broth from this cooled flask was used as a 5% inoculum to initiate fermentation in KE, KW and KEM production media.

(B) A 250 ml production flask containing 54 ml of production media (KE, KW or KEM) was aseptically treated with 2.7 ml cold seed medium from (A). The production flask was agitated at 28° C. on a 220 rpm shaker (2" throw) for 96 hours, after which time the broth was harvested.

EXAMPLE 2

*Streptomyces griseus* ATCC No. 39208 was used to inoculate 54 ml of seed medium KE in a 250 ml flask. The seed flask was agitated at 28° C. on a 220 rpm (2" throw) shaker for 24 hours. A 10 ml portion of this seed broth was used to inoculate, using aseptic techniques, 500 ml of seed medium KE in a baffled two liter Erlenmeyer flask. After 48 hours incubation at 28° C. with 220 rpm agitation, the entire contents of the flask was used to inoculate 415 liters of production medium KW in a fermentor. The fermentor was operated for 150 hours at 28° C. with 400 rpm agitation and an air flow of 3 liters per minute after which time the broth was harvested as described in Example 3.

EXAMPLE 3

Isolation and Characterization of Tejeramycin

The broth from Example 2 (416 L), pH 7.9, and 16 kg of Supercel was filtered through an 18″ filter press. The filtrate was adjusted to pH 4.4–4.6 with 3.6 N sulfuric acid and adsorbed onto 28 L of Dowex 50×2, 50–100 mesh resin, sodium cycle at 2.5 L/min. The resin was washed with 50 L of water. The resin was first eluted with 0.1 M sodium phosphate, pH 6.5 at 2.5 L/min. Six 18 L-fractions were collected (Fractions 1–6). The resin was then eluted with 2% pyridine in distilled water at 2.5 L/min. Ten 15 L-fractions were collected (Fractions 7–16). Based on agar disc diffusion assay against *Pseudomonas aeruginosa* MB2787, fractions 7 to 15 were combined, adjusted to pH 6.8 and concentrated to 5.7 L by reverse osmosis. The concentrate contained 214 g of total solids.

The concentrate, pH 6.8, was adsorbed on 2 L of Amberlite XAD-2 resin, 20–50 mesh, at 100 ml/min. The resin was washed with 4 L of distilled water, followed by 4 L of 5% acetonitrile in water. The Tejeramycin complex was eluted with 16 L of 15% acetonitrile in water at 100 ml/min. Eight 2 L-fractions were collected. Fractions 1–6 (total solids 14.4 g) were combined and concentrated. The concentrate was reconstituted to 550 ml with 0.1 M sodium phosphate pH 6.5 in 15:85 acetonitrile-water. The solution was chromatographed in 2 portions on 2 L Dowex 50×2, 200–400 mesh resin on the sodium cycle. Eluting solvent was 0.1 M sodium phosphate pH 6.5 in 15:85 acetonitrile-water and the flow rate was 50 ml/min. Fractions 1 and 2 were each 500 ml. Fractions 3 through 18 were each 250 ml. Fraction 19 was 1 L. Fractions 7–16 were pooled as the rich cut. The rich cuts from the two Dowex 50×2 runs were combined and concentrated to 1 L. The 1 L concentrate was adsorbed on 800 ml of Amberlite XAD-2 resin, 20–50 mesh at 40 ml/min. The resin was washed with 2 L of water and the tejeramycin complex was eluted with 15% acetonitrile in water. Eluate was collected in 12 500 ml-fractions. Fractions 1–9 were combined and concentrated to 250 ml. About 5 ml of acetonitrile was added to dissolve precipitated material. The final solution was lyophilized to afford 5.43 g of tan colored solid.

EXAMPLE 4

Separation of Tejeramycin Components A thru G

A 4.9 g sample of the tan colored solid isolated in Example 3 was chromatographed at room temperature on 2 L of LiChroprep RP-18 resin (E. Merck, 25–40 micron) in 3:7 methanol—0.074 M potassium acetate buffer, pH 4.0. The flow rate was about 6.5 ml/min. After a forerun cut of 1.26 L, fractions were collected every three minutes. After 432 fractions had been collected, the column was eluted with 4 L of 6:4 methanol—0.074 M potassium phosphate buffer, pH 7.0 (fraction 433). Column effluent was continuously monitored at 258 nm using a Micromeritics Instruments Corp. Model 785 C ultraviolet detector equipped with a 1 mm path length flow cell. A number of distinct UV active peaks eluted from the column. Agar disc-diffusion assay showed that effluent in seven of these peaks had antibacterial activity against *Pseudomonas aeruginosa* MB 2787 and these peaks were labelled Tejeramycin Components A through G (See the FIGURE). Fractions were then assayed by HPLC at 60° C. and 258 nm using a 10 micron ES Industries $C_{18}$ column (4.6 mm×30 cm) and isocratic mixtures of acetonitrile and 0.1 M ammonium formate buffer (pH 2.9) as eluant. The percentage of acetonitrile varied from 10% to 13% depending upon the lypophilicity of the component examined. Based on the assay results, fractions were combined as shown in Table III.

TABLE III

| | Chromatography of Tejeramycin Components A through G. | | | | |
|---|---|---|---|---|---|
| Rich Cut | Combined Fractions | Tejeramycin Component | Wt. | UV Data | |
| 1 | 35–55 | A | 160 mg | 254 | 175 |
| 2 | 80–115 | B | 257 mg | 253 | 178 |
| 3 | 125–155 | C | 373 mg | 257 | 191 |
| 4 | 156–190 | C | 389 mg | 257 | 173 |
| 5 | 240–285 | D | 550 mg | 251 | 168 |
| 6 | 286–330 | E | 294 mg | 251 | 191 |
| 7 | 331–420 | F | 719 mg | 258 | 243 |
| 8 | 421–432 | G | 90 mg | 257 | 198 |
| 9 | 433 | F & G | 867 mg | 251 | 157 |

Each rich cut was concentrated at pH 6.8 to remove methanol, adjusted to pH 4.5, and adsorbed at 10 ml/min onto 100 ml of Dowex 50×2, 50–100 mesh resin, sodium cycle. The resin was washed with 400 ml of water and activity was eluted with 2:20:80 pyridine-methanol-water. Fractions of 20 ml were collected and assayed by HPLC. The combined rich cut was evaporated to dryness and lyophilized from water at pH 6.8.

Tejeramycin components F and G in Rich Cut 9 were separated as follows. A 660 mg sample of Rich Cut 9, dissolved in 40 ml of 3:7 methanol-water, was chromatographed on 175 ml of LiChroprep RP-18 resin (E. Merck, 25–40 micron) in 3:7 methanol-water. The flow rate was 3 ml/min. and fractions were 10 ml each. After fraction 42, a convex exponential solvent gradient was used. The gradient ran from 3:7 methanol-water to a limiting value of 1:1 methanol-water, approximately reached after a total of 110 fractions had been collected. The antibiotic eluted in five distinct bands based on bio-assay and UV monitoring of column effluent at 258 nm. HPLC analysis of the fractions showed that several bands contained multiple substances. Fractions were combined as shown in Table IV.

TABLE IV

| | Separation of Tejeramycin Components F and G from Rich Cut 9 | | | | |
|---|---|---|---|---|---|
| Rich Cut | Combined Fractions | Tejeramycin Component | Wt. | UV Data | |
| 9a | 59–70 | F | 89 mg | 252 | 217 |
| 9b | 71–81 | G | 116 mg | 252 | 170 |
| 9c | 82–88 | G | 60 mg | 255 | 169 |
| 9d | 89–96 | G | 78 mg | 252 | 123 |
| 9e | 97–106 | G | 45 mg | 255 | 158 |

Tejeramycin components A–G were analyzed by HPLC under the following conditions:
Dupont Industries Zorbax ODS column (4.6 mm×25 cm), 10 micron. operated of 40° C.
15:25 acetonitrile—0.1 M ammonium formate buffer, pH 2.9
flow rate: 1.2 ml/min.

UV of column effluent monitored at 258 nm.

Results of this HPLC analysis are summarized in Table V.

TABLE V
HPLC Analyses of Tejeramycin Components

| Component | Rich Cut | Retention Time Major Peaks | Minor Peaks |
|---|---|---|---|
| A | 1 | * | |
| B | 2 | 376 sec | 311 sec |
| C complex | 3 | 457 sec | 249 sec |
| | | | 299 sec |
| | | | 341 sec |
| | 4 | 448 sec | 297 sec |
| D | 5 | 495 sec | |
| E | 6 | 662 sec | |
| F complex | 7 | 536 sec | |
| | | 645 sec | |
| | 8 | 535 sec | 342 sec |
| | 9a | 532 sec | 341 sec |
| | | | 641 sec |
| | | | 816 sec |
| G complex | 9b | 744 sec | |
| | | 1008 sec | |
| | 9c | 817 sec | 1188 sec |
| | | 1044 sec | |
| | 9d | 1189 sec | |
| | | 1609 sec | |
| | 9e | 1602 sec | |
| | | 1311 sec | |

*retention time of major peak in Component A was 349 sec. as compared to 689 sec for Component B under the following conditions: 10 micron ES Industries $C_{18}$ column (4.6 mm × 30 cm) operated at 60° C. in 7:93 acetonitrile - 0.1 M ammonium formate pH 2.9 with a flow rate of 1.2 ml/min., 258 nm UV monitoring of column effluent.

Antibiotics A38533A1 and A38533B, disclosed in U.S. Pat. No. 4,180,564, may belong to the same general class of antibiotics as Tejeramycin. However the Tejeramycin complex is distinct from A38533A1 and A38533B since HPLC retention times of the latter two antibiotics (see Table VI) do not match any of the retention times of the major or minor peaks for the Tejeramycin components A to G. (See Table V).

TABLE VI
HPLC ANALYSIS OF A38533A1 AND A38533B*

| Component | Retention Time Major Peaks |
|---|---|
| A38533A1 | 435 sec |
| A38533B | 1495 sec |
| | 1991 sec |

*HPLC conditions were the same as for analyses of components B-G of TABLE V.

Thin layer chromatographic (TLC) analyses of the lyophilized Tejeramycin components A-G described in Tables III and IV were performed. Two different TLC systems were used:

(1) E. Merck silica gel 60F-254 in 4:1:1 butanol-acidic acid-water and (2) Quanta reverse phase plates $KC_{18}$ in 6:4 methanol—0.1 M ammonium formate pH 2.9.

Test concentrations of Tejeramycin Components A and B were 33 mg/ml and 20 mg/ml in water respectively. Components C through G were tested at 10 mg/ml. All components were applied as a 3 μl spot to the TLC plates. After development and drying of the plates, spots were visualized using the following methods and reagents:

(1) observation under short ultraviolet irradiation. Dark spots on silica gel 60F and $KC_{18}$ reverse phase plates.

(2) naphthalene-1,3-diol/$H_2SO_4$. Blue spots on silica gel 60F and $KC_{18}$ reverse phase plates.

(3) Pauly reagent. Orange to brown spot on silica gel 60F. Not all of the $R_f$ values listed below necessarily correspond to antibiotic entities, but likely many do since most respond similarly to visualization methods 1, 2 and 3 as does purified antibiotic Tejeramycin -Cl (vida infra). The TLC results are shown in Table VII.

TABLE VII
TLC Analyses of Tejeramycin Components[1]

| Rich Cut | Component | Silica Gel 60F[2] | $KC_{18}$[3] |
|---|---|---|---|
| 1 | A | 0.22 | 0.82 |
| 2 | B | 0.16; <u>0.32</u> | 0.83 |
| 3 | C | 0.21; 0.48; 0.51; 0.59 | <u>0.80</u> ; 0.83 |
| 4 | C | 0.26; <u>0.51</u> | <u>0.79</u> ; 0.83 |
| 5 | D | 0.44 | 0.78 |
| 6 | E | <u>0.59</u> ; 0.71 | 0.77 |
| 7 | F | <u>0.46</u> ; 0.54; 0.57 | 0.76 |
| 8 | F | 0.49 | 0.77 |
| 9a | F | 0.39; <u>0.49</u> ; 0.68 | 0.77 |
| 9b | G | 0.56 | <u>0.70</u> ; 0.68 |
| 9c | G | 0.54 | 0.69 |
| 9d | G | 0.49; 0.66 | 0.67 |
| 9e | G | <u>0.50</u> ; 0.65 | 0.66 |

[1]$R_f$ value of major spots are underlined.
[2]Solvent system: 4:1:1 butanol-acetic acid-water.
[3]Solvent system: 6:4 methanol - 0.1 M ammonium formate pH 2

The Tejeramycin components A thru G were tested in vitro against *Pseudomonas aeruginosa* MB 2787 by conventional agar disc diffusion assay. The in vitro test results are summarized in Table VIII.

TABLE VIII

In Vitro Potency of Tejeramycin Components A-G against *Pseudomonas aeurginosa* MB 2787
Definition of Unit of Activity: 0.1 ml of a solution of one unit of activity in 1 ml of water on a ¼" disc gives a 25 mm zone of inhibition against *Pseudomonas aeurginosa* MB 2787.

| Rich Cut | Tejeramycin Component | Potency vs. MB 2787 Units/mg. |
|---|---|---|
| 1 | A | 0.60 |
| 2 | B | 2.0 |
| 3 | C | 2.0 |
| 4 | C | 1.6 |
| 5 | D | 4.7 |
| 6 | E | 5.5 |
| 7 | F | 11.2 |
| 8 | F | 11.4 |
| 9a | F | 10.2 |
| 9b | G | 3.9 |
| 9c | G | 7.8 |
| 9d | G | 4.5 |
| 9e | G | 8.8 |

The in vitro activity of two Tejeramycin components, E and F, against gram positive and gram negative organisms is shown in Table IX.

TABLE IX

In Vitro Potency of Tejeramycin components E (Rich Cut 6) and F (Rich Cut 7) against Gram Positive and Gram Negative Organism

| | Inhibition Zone Diameter, mm | |
|---|---|---|
| Organism, MB (ATCC) | E 1.3 mg/ml | F 0.9 mg/ml |
| *Bacillus* sp. 633 | 0 | 0 |
| *Pseudomonas aeruginosa* 979 | 26 | 24 |
| *Staphlococcus aureus* 108 (6538P) | 10 | 10 |
| *Bacillus subtilis* 964 (6633) | 0 | 6 |

TABLE IX-continued

In Vitro Potency of Tejeramycin components E (Rich Cut 6) and F (Rich Cut 7) against Gram Positive and Gram Negative Organism

| | Inhibition Zone Diameter, mm | |
|---|---|---|
| | E | F |
| Organism, MB (ATCC) | 1.3 mg/ml | 0.9 mg/ml |
| *Sarcina lutea* 1101 (9341) | 0 | 6 |
| *Salmonella gallinarum* 1287 | 0 | 0 |
| *Vibrio percolans* 1272 (8461) | 5 | 9 |
| *Proteus vulgaris* 838 | 0 | 0 |
| *Escherichia coli* 1418 | 23 | 23 |
| *Pseudomonas stutzeri* 1231 (11607) | 0 | 0 |
| *Klebsiella pneumoniae* 1264 | 0 | 7 |
| *Enterobacter aerogenes* 835 | 0 | 0 |
| *Pseudomonas aeruginosa* 2824 | 23 | 24 |
| *Escherichia coli* 60 | 0 | 0 |
| *Bacillus subtilis* 964 in Chem. Defined Agar | 26 | 26 |
| *S. aureus* 108 in Chem. Defined Agar | 26 | 26 |
| *Micrococcus flavus* 369 | 10 | 5 |
| *Streptomyces sp.* 4798 | 17 | 21 |
| *Staph lococcus aureus* 2983 | 15 | 11 |

The in vivo activities of Tejeramycin, components A through G were determined against *Pseudomonas aeruginosa* MB 2835 infections in mice. Experimental systemic infections were produced in CD 1 female mice (Charles River Breeding Labs., Wilmington, Ma.), average body weight 19–22 grams, by the intraperitoneal (i.p.) injection of a suitably diluted overnight culture of *Pseudomonas aeruginosa* MB-2835 in brain heart infusion broth (Difco). The challenge dose varied from about 11–50 $LD_{50}$'s $LD_{50}$=median lethal dose, the dose that should kill 50% of the infected, untreated mice). Under these conditions, the infected, untreated mice died within 48 hours.

The antibiotics were administered as aqueous solutions by intraperitoneal or subcutaneous (s.c.) injection at 0 and 6 hours after infection. At least four different dose levels of the antibiotics were used; each dose group consisted of five mice. All animals were observed for a period of 7 days after which the median effective dose, $ED_{50}$, (the dose that should protect 50% of the infected, treated mice) was calculated by the method of Knudsen and Curtis, see: "The Use of the Angular Transformation in Biological Assays," *J. Amer. Statist. Assoc.* 42: 282–296, 1947.

From rich cuts 1–9e described in Tables III and IV, a series of seven samples were prepared for in vivo evaluation. Sample composition as well as in vivo results are summarized in Table X. Carbenicillin and gentamicin were included as controls.

TABLE X

In Vivo Activity of Tejeramycin Components A–G against *Pseudomonas aeruginosa* MB 2835

| Sample Composition* (% of in vitro potency) | Tejera- mycin Component | $ED_{50}$ (mg)*** i.p. | s.c. | s.c./ i.p.** |
|---|---|---|---|---|
| Example A: | | | | |
| Rich cut 2 (50%) Rich cut 3 (50%) | B + C | 0.53 | 12.5 | 24 |
| Rich cut 3 (30%) Rich cut 4 (70%) | C complex | 0.64 | 14.5 | 23 |
| Rich cut 5 (100%) | D | 0.063 | 5.5 | 87 |
| Carbenicillin | | 5.31 | 17.1 | 3.2 |
| Gentamicin | | 0.013 | 0.30 | 23 |
| Example B: | | | | |
| Rich cut 6 (100%) | E | 0.050 | 1.21 | 24 |
| Rich cut 7 (100%) | F complex | 0.017 | 0.98 | 58 |
| Rich cut 8 (50%) Rich cut 9a (50%) | F complex | 0.012 | 1.75 | 146 |
| Rich cut 9b (25%) Rich cut 9c (25%) Rich cut 9d (25%) Rich cut 9e (25%) | G complex | 0.019 | 3.50 | 184 |
| Carbenicillin | | 4.14 | 6.04 | 1.5 |
| Gentamicin | | 0.0063 | 0.125 | 20 |

*absolute in vitro potencies of individual rich cuts are summarized in Table VIII.
**s.c./i.p. - subcutaneous/intraparitoneal $ED_{50}$ administration ratio
***multiplied by two doses The results of the in vivo experiments demonstrate that antibiotic Tejeramycin components A through G are especially useful antibiotics against Pseudomonas infections.

Based on the in vitro and in vivo results discussed above, a daily effective dosage of the antibiotics Tejeramycin for the treatment of gram negative or gram positive infections in an animal, especially in a human, would be on the order of from 1.2 mg/kg to 64 mg/kg for intraparitoneal (i.p.) administration and from 98 mg/kg to 350 mg/kg for subcutaneous administration. Appropriate dosage forms would include solutions, suspensions and emulsions.

EXAMPLE 5

Isolation of Essentially Pure Antibiotic Tejeramycin-F1

A 200 mg sample of Tejeramycin-F complex, rich cut 7 of Example 4, was dissolved in 10 ml of 1:9 acetonitrile—0.1 M ammonium formate pH 2.9. The solution was chromatographed in twenty 0.5 ml aliquots on a 0.69 cm×60 cm column of ES Industries $C_{18}$ resin, 40–50 micron, operated at 60° C. The solvent system was 12:88 acetonitrile—0.1 M ammonium formate pH 2.9. The flow rate was 5 ml/min and column effluent was monitored at 258 nm. The effluent fractions corresponding to the peak with retention time 536 sec in Table V were collected, combined and concentrated to dryness. The residue was dissolved in water adjusted to pH 4, and adsorbed on 25 ml of Dowex 50×2, 50–100 mesh resin on the sodium cycle at 3 ml/min. The resin was washed with 120 ml of water and the antibiotic was eluted with 2:20:80 pyridine-methanol-water. The eluate (120 ml) was evaporated to dryness. The residue was taken up in a small volume of water, adjusted to pH 6.4 and lyophilized to yield 47.1 mg.

The lyophilized solid was dissolved in 10 ml of water and adsorbed on a column of 10 ml of Amberlite XAD-2 resin at 1 ml/min. The column was washed with several column volumes of water and the antibiotic was eluted with 50 ml of 2:8 acetonitrile-water. The eluate was concentrated to 3 ml and lyophilized to afford 15.5 mg of essentially pure Tejeramycin-F1 as a white solid. The ultraviolet spectrum of the white solid in water exhibited the following characteristics: λ max ($A^{1}\%$) 215 nm, sh (340), 258 nm (206).

EXAMPLE 6

Isolation of Essentially Pure Antibiotic Tejeramycin-F2

About 32 mg of Tejeramycin-F complex, rich cut 8 of Example 4, was dissolved in 2.5 ml of warm 1:9 acetonitrile-water in three portions and chromatographed on a 0.69 cm×50 cm column of E.S. Industries $C_{18}$ resin, 40-50 micron, operated at 60° C. The eluting solvent was 12:88 acetonitrile—0.1 M ammonium formate pH 2.9. The flow rate was 5 ml/min and column effluent was monitored at 258 nm. The effluent fraction corresponding to the peak with retention time 535 sec in Table V were collected and combined. The pooled rich cut was concentrated to dryness and dissolved in 50 ml of water. The solution was adjusted to pH 4.5 and adsorbed on 10 ml of Dowex 50×2 50-100 mesh resin on the sodium cycle at 1 ml/min. After washing the resin with 30 ml of water, the antibiotic was eluted from the resin with 55 ml of 2:20:80 pyridine-methanol-water. The eluate was concentrated to dryness. The residue was dissolved in 20 ml of water and the pH was adjusted to 6.7. The solution was adsorbed on 5 ml of Amberlite XAD-2 resin at 0.5 ml/min. The resin was washed with water and the antibiotic eluted with 40 ml of 2:8 acetonitrile-water. The eluate was concentrated to 2 ml and lyophilized to afford 14.6 mg of essentially pure antibiotic Tejeramycin-F2 as a white solid.

The ultraviolet spectrum of Tejeramycin-F2 in water exhibited the following characteristics: $\lambda max$ ($A^{1\%}$) 215 nm sh (330), 258 nm (205).

EXAMPLE 7

Fermentation to Produce Tejeramycin Component Cl

A 400-L fermentation batch was grown under conditions similar to those of Example 2. During fermentation, time samples of whole broth were collected and bioassayed by agar disc diffusion against *Pseudomonas aeruginosa* MB2824. A 19-L sample collected after 72 hours and a 57-L sample collected after 93 hours (total) were pooled. From this pooled broth, Tejeramycin component Cl was isolated as described in Example 8.

EXAMPLE 8

Isolation of Antibiotic Component Tejeramycin-Cl

The 76 L of pooled broth from Example 7 was filtered through celite. The mycelial cake was washed with sufficient water to bring the total filtrate volume to 76 L. The filtrate was adjusted to pH 4.5 and adsorbed on 4.5 L of Dowex 50×2, 50-100 mesh resin on the sodium cycle at 450 ml/min. The column was washed successively with 12 L of distilled water, 14 L of 0.1 M sodium phosphate buffer at pH 6.5, 8 L of phosphate buffer at pH 7.0 and 12.5 L of phosphate buffer at pH 8.5. The column was then eluted with 24 L of 2% pyridine in water at 450 ml/min. Effluent was collected in fractions. Fractions 1-4 were each 2 L, fractions 5-7 were each 4 L. Agar disc diffusion assay against *Pseudomonas aeruginosa* MB 2824 showed the activity to be in pH 8.5 phosphate wash and fractions 1-4. The pH 8.5 wash was adjusted to pH 6.5 and concentrated to 4 L. Fractions 1-4 were combined, concentrated at pH 8.5 to 1 L, and adjusted to pH 6.5. The two concentrates were successively adsorbed on 500 ml of Amberlite XAD-2, 20-50 mesh resin, at 20 ml/min. The resin was washed with 2.5 L of distilled water, 2 L of 5:95 acetonitrile-water, and 1.5 L of 10:90 acetonitrile-water. Activity was eluted with 1.5 L of 15:85 acetonitrile-water collected in 250 ml fractions (fractions 1-6) and with 1.5 L of 20:80 acetonitrile-water collected in 500 ml fractions (fractions 7-9). Based on agar disc diffusion assay against *Pseudomonas aeruginosa* MB 2824, fractions 2-8 were combined as the rich cut, which was then concentrated to 100 ml. The concentrate was adjusted to pH 8.3, washed twice with 70 ml of ethyl acetate, and brought to pH 3. A precipitate formed which was removed by centrifugation. The clear centrifugate was adjusted to pH 7 and lyophilized to afford 1.9 g of bioactive solids.

A 1.79 g sample of the lyophilized bioactive solids was dissolved in 50 ml of water and applied at pH 7 to 1 L of acid-washed Florosil (Fisher Scientific), 60-100 mesh. The column was developed successively with 3.4 L of distilled water, 2.6 L of 5:95 acetone-water, and 2 L of 10:90 acetone-water. The flow rate was 30 ml/min and effluent was collected in 200 ml fractions. Recovery of bioactivity was about 80%, about 13% of which eluted with water and the remainder with 5:95 acetone-water. All fractions with anti-Pseudomonas plate activity were combined and concentrated to remove acetone. Dissolved inorganics arising from the Florosil adsorbent were removed by adsorbing the concentrate at pH 7 on 100 ml of Amberlite XAD-2, 20-40 mesh resin. The resin was washed with water and with 5:95 acetonitrile-water. The antibiotic was eluted with 15:85 acetonitrile-water. The eluate was 500 ml and contained 0.49 g of total solids.

A 435 ml aliquot of the above XAD-2 eluate (0.39 g total solids) was concentrated to dryness, dissolved in 25 ml of 15:85 acetonitrile-water; and chromatographed on 190 ml of E. Merck LiChroprep RP-18, 25-40 micron resin in 35:65 methanol-water at 3 ml/min. Fractions 1-75 were 20 ml each. Fraction 76 was 500 ml. The antibiotic activity peaked in fraction 20. Fractions 14-30 were combined as the rich cut, concentrated, and lyophilized to give 0.25 g of light tan solid.

Approximately 80 mg of the light tan solid was further purified by dissolution in 15 ml of 15:85 acetonitrile-water and chromatography in the same solvent at 2 ml/min on 235 ml of pulverized Amberlite XAD-2, 400 mesh resin. Effluent was collected in 10 ml fractions. Fractions were assayed by HPLC and by agar disc diffusion against *Pseudomonas aeruginosa* MB 2824. Fractions 29-33 were combined, concentrated, and lyophilized to yield 20 mg of essentially pure Tejeramycin antibiotic component Cl as a white fluffy solid.

HPLC analysis of this Tejeramycin component using the system described in Table V exhibited a single dominant peak with a retention time of 475 sec. The retention time of this antibiotic was different than retention times for major and minor peaks in Tejeramycin components A-G listed in Table VI. Because of the similarity of the retention time of this antibiotic with those of the Tejeramycin-C complex, the antibiotic was assigned to this group and designated Tejeramycin-Cl.

The ultraviolet spectrum of Tejeramycin-Cl 0.1 M pH 7 sodium phosphate exhibited the following characteristics: $\lambda max$ ($A^{1\%}$) 215 nm sh (354), 258 nm (200).

The TLC $R_f$ values of Tejeramycin-Cl on silica gel 60 F-254 and $KC_{18}$ in the solvent systems defined in Table VI were 0.56 and 0.80 respectively. Table XI shows the TLC visualization characteristics of Tejeramycin components -$C_1$.

TABLE XI

TLC Visualization Characteristics of Tejeramycin-Cl

| Visualization Method | Response |
| --- | --- |
| Short UV fluorescence quench | + |
| Iodine | + |
| $H_2SO_4$ | − |
| Anisaldehyde/$H_2SO_4$ | + |
| Naphthalene-1,3-diol/$H_2SO_4$ | + blue |
| Triphenyltetrazolium chloride | − |
| Pauly Reagent | + brown |
| Ninhydrin | − or v. weak |
| Erlich Reagent | − |
| 2,4-dinitrophenylhydrazine | − |
| Molybdate/$H_2SO_4$ | − |

The in vitro potency of Tejeramycin component C-1 against *Pseudomonas aeruginosa* MB 2728 was 8.3 units/mg as defined in Table VIII.

What is claimed is:

1. The antibiotic complex produced by the controlled aerobic fermentation of a strain of *Streptomyces griseus* selected from ATCC No. 39208 or 39209 in an assimilable aqueous nutrient medium until a sufficient amount of said antibiotic is accumulated for isolation.

2. The process of producing the antibiotic complex of claim 1, which comprises cultivating an antibiotic-producing strain of the genus Streptomyces selected from *Streptomyces griseus* ATTC No. 39208 or 39209 under controlled aerobic conditions in an aqueous nutrient medium until a sufficient amount of said antibiotic complex is accumulated for isolation.

3. A pharmaceutical composition containing an antibacterially effective amount of the antibiotic complex of claim 1 and a pharamaceutical carrier.

4. A method of treating gram negative or gram positive infections in animals, which comprises administering by injection in said animal an antibacterially effective amount of the antibiotic complex of claim 1 in a pharamaceutical carrier.

5. A method of treating Pseudomonas infections in animals, which comprises administering by injection in said animal an antibacterially effective amount of the antibiotic complex of claim 1 in a pharmaceutical carrier.

* * * * *